US010617571B2

(12) United States Patent
Quinn

(10) Patent No.: US 10,617,571 B2
(45) Date of Patent: *Apr. 14, 2020

(54) PRE-CUT STRIPS OF KINESIOLOGY TAPE

(75) Inventor: Reed Quinn, Highland, UT (US)

(73) Assignee: KT Health, LLC, Lindon, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 13/188,333

(22) Filed: Jul. 21, 2011

(65) Prior Publication Data

US 2011/0275969 A1 Nov. 10, 2011

Related U.S. Application Data

(63) Continuation-in-part of application No. 12/626,355, filed on Nov. 25, 2009, now Pat. No. 9,308,115.

(Continued)

(51) Int. Cl.
A61F 13/02 (2006.01)
A61F 5/40 (2006.01)
A61F 13/00 (2006.01)

(52) U.S. Cl.
CPC ............ *A61F 13/0276* (2013.01); *A61F 5/40* (2013.01); *A61F 13/00059* (2013.01); *A61F 13/025* (2013.01); *A61F 13/0259* (2013.01)

(58) Field of Classification Search
CPC ...... A61L 15/58; A61F 13/02; A61F 13/0253; A61F 13/0259; A61F 13/0273;

(Continued)

(56) References Cited

U.S. PATENT DOCUMENTS 1,441,708 A 1/1923 Overbury
2,646,040 A * 7/1953 Stanton ............... A61F 13/0203
602/58

(Continued)

FOREIGN PATENT DOCUMENTS

BE 1002779 6/1991
CN 101616645 A 12/2009

(Continued)

OTHER PUBLICATIONS

Office Action from Chinese Patent Application 201280044120.0 dated Nov. 3, 2014.

(Continued)

*Primary Examiner* — Ophelia A Hawthorne
*Assistant Examiner* — Caitlin A Carreiro
(74) *Attorney, Agent, or Firm* — Maschoff Brennan; Paul G. Johnson

(57) ABSTRACT

A pre-cut strip of kinesiology tape. The pre-cut strip of kinesiology tape includes a fabric. The fabric includes a weave of fibers, where the fibers include an elastic fiber covered by a covering material. The fabric also includes a first end and a second end, where the second end is opposite the first end. The fabric further includes one or more rounded corners. The pre-cut strip of kinesiology tape also includes a longitudinal cut in the fabric. The longitudinal cut passes through at least a portion of the fabric and extends from the first end to a pre-determined distance from the second end. The pre-cut strip of kinesiology tape also includes adhesive on a first surface of the fabric, where the adhesive is configured to adhere the fabric to a human body.

20 Claims, 9 Drawing Sheets

Related U.S. Application Data

(60) Provisional application No. 61/200,400, filed on Nov. 26, 2008.

(58) Field of Classification Search
CPC . B32B 27/12; B32B 2555/00; B32B 2307/51; B32B 5/024; C09J 2201/28; C09J 2201/40
USPC ............ 602/44, 52, 54, 55, 57, 58, 59, 903; 523/111, 105, 118, 113, 114; 428/175, 428/193, 196, 214
See application file for complete search history.

(56) References Cited

U.S. PATENT DOCUMENTS

| | | | |
|---|---|---|---|
| 2,957,475 | A | 10/1960 | Drake |
| 3,038,295 | A | 6/1962 | Humphreys |
| 3,342,028 | A | 9/1967 | Kanji et al. |
| 3,355,974 | A | 12/1967 | Carmichael |
| 3,387,451 | A | 6/1968 | Cape et al. |
| 3,530,494 | A | 9/1970 | Baratta |
| 3,716,132 | A | 2/1973 | Lewyckyj |
| 3,965,786 | A | 6/1976 | D'Luhy |
| 3,989,041 | A | 11/1976 | Davies |
| 4,215,687 | A | 8/1980 | Shaw |
| 4,654,254 | A | 3/1987 | Gerry et al. |
| 4,735,342 | A | 4/1988 | Goldstein |
| 4,782,196 | A | 11/1988 | Ukai |
| 5,240,775 | A | 8/1993 | Zimmer |
| 5,488,889 | A | 2/1996 | Kang |
| 5,496,605 | A | 3/1996 | Augst et al. |
| 5,537,905 | A | 7/1996 | Zimmer et al. |
| 5,782,496 | A | 4/1998 | Casper et al. |
| 5,755,681 | A | 5/1998 | Plews |
| 5,792,091 | A * | 8/1998 | Staudinger ............... A61F 13/10 602/20 |
| 5,861,348 | A * | 1/1999 | Kase ..................... A61F 13/025 442/184 |
| 5,938,631 | A | 8/1999 | Colman |
| 5,972,091 | A | 10/1999 | Giesfeldt et al. |
| 5,981,823 | A | 11/1999 | Turngren |
| 6,007,458 | A | 12/1999 | Giacometti |
| 6,213,343 | B1 | 4/2001 | Damikolas |
| 6,422,848 | B1 | 7/2002 | Allen et al. |
| 6,447,470 | B2 | 9/2002 | Bodenshatz et al. |
| 6,756,519 | B2 | 7/2004 | Johnson et al. |
| 6,769,428 | B2 | 8/2004 | Cronk |
| 6,953,602 | B2 * | 10/2005 | Carte ................... A61F 13/023 427/208.4 |
| 6,953,620 | B2 * | 10/2005 | Schneider et al. ......... 428/304.4 |
| 7,012,170 | B1 | 3/2006 | Tomaiuolo |
| 7,146,893 | B2 | 12/2006 | Aichele |
| 7,594,461 | B2 | 9/2009 | Aichele et al. |
| D604,856 | S | 11/2009 | Arbesman et al. |
| D607,114 | S | 12/2009 | Arbesman et al. |
| D608,007 | S | 1/2010 | Arbesman et al. |
| D608,453 | S | 1/2010 | Arbesman et al. |
| D608,894 | S | 1/2010 | Arbesman et al. |
| D608,896 | S | 1/2010 | Arbesman et al. |
| D608,893 | S | 2/2010 | Arbesman et al. |
| D609,354 | S | 2/2010 | Arbesman et al. |
| D612,505 | S | 3/2010 | Arbesman et al. |
| D612,506 | S | 3/2010 | Arbesman et al. |
| D612,507 | S | 3/2010 | Arbesman et al. |
| D612,508 | S | 3/2010 | Arbesman et al. |
| D612,944 | S | 3/2010 | Arbesman et al. |
| D613,414 | S | 4/2010 | Arbesman et al. |
| D613,415 | S | 4/2010 | Arbesman et al. |
| D616,553 | S | 5/2010 | Arbesman et al. |
| D616,998 | S | 6/2010 | Arbesman et al. |
| D621,518 | S | 8/2010 | Arbesman et al. |
| D622,403 | S | 8/2010 | Arbesman et al. |
| 7,790,420 | B2 | 9/2010 | Hart et al. |
| D625,422 | S | 10/2010 | Arbesman et al. |
| D625,825 | S | 10/2010 | Arbesman et al. |
| 8,216,415 | B2 | 7/2012 | Quinn |
| 8,617,199 | B2 | 12/2013 | Eull et al. |
| 9,308,115 | B2 | 4/2016 | Quinn |
| 2002/0040202 | A1* | 4/2002 | Levin ................... A61F 13/0203 602/43 |
| 2003/0069530 | A1 | 4/2003 | Satou et al. |
| 2003/0183053 | A1 | 10/2003 | Amend et al. |
| 2006/0065098 | A1 | 3/2006 | Cranna |
| 2006/0206047 | A1 | 9/2006 | Lampe |
| 2007/0010777 | A1 | 1/2007 | Dunshee et al. |
| 2007/0073205 | A1 | 3/2007 | Hull et al. |
| 2008/0043085 | A1 | 2/2008 | Einhorn |
| 2008/0299855 | A1 | 12/2008 | Morihashi |
| 2009/0182256 | A1 | 7/2009 | Lin |
| 2010/0003431 | A1* | 1/2010 | Raybuck ................ B32B 1/02 428/34.2 |
| 2010/0016771 | A1 | 1/2010 | Arbesman et al. |
| 2010/0227102 | A1 | 9/2010 | Keener et al. |
| 2010/0289747 | A1 | 11/2010 | Quinn |
| 2010/0298747 | A1 | 11/2010 | Quinn |
| 2014/0102632 | A1 | 4/2014 | Quinn |

FOREIGN PATENT DOCUMENTS

| | | |
|---|---|---|
| CN | 102068338 | 5/2011 |
| DE | 825 448 C | 12/1952 |
| DE | 1221091 | 7/1996 |
| FR | 2 896 808 A1 | 8/2007 |
| GB | 953855 | 4/1964 |
| JP | 2004 248842 A | 9/2004 |
| JP | 2008-136656 | 6/2008 |
| KR | 10-0802172 | 2/2008 |
| WO | WO2013011385 A2 | 1/2013 |

OTHER PUBLICATIONS

Office Action from U.S. Appl. No. 13/188,319, dated Dec. 11, 2014.
Office Action from U.S. Appl. No. 12/626,355, dated Jan. 22, 2015.
Office Action from Canadian Patent Application No. 2,845,061, dated Feb. 16, 2015.
Office Action from Korean Patent Application No. 10-2014-7004559, dated Jan. 6, 2015 (with English translation).
U.S. Appl. No. 12/626,355, filed Nov. 25, 2009, Quinn.
U.S. Appl. No. 13/188,319, filed Jul. 21, 2011, Quinn.
U.S. Appl. No. 13/188,327, filed Jul. 21, 2011, Quinn.
U.S. Appl. No. 14/135,416, filed Dec. 19, 2013, Quinn.
Office Action from U.S. Appl. No. 13/188,319 dated May 6, 2014.
Office Action from U.S. Appl. No. 12/626,355 dated May 23, 2014.
Office Action from U.S. Appl. No. 12/626,355 dated Aug. 29, 2013.
Office Action from U.S. Appl. No. 13/188,327 dated Nov. 8, 2013.
Kinesio Taping Perfect Manual.
International Search Report from PCT/US2015/045972, dated Nov. 6, 2015.
Written Opinion from PCT/US2015/045972, dated Nov. 6, 2015.
Office Action from Korean Patent Application No. 10-2014-7004559, dated Nov. 23, 2015.
Office Action from Chinese Patent Application No. 201010566803.5, dated Dec. 10, 2015.
Examiner's Report from European Patent Application No. 12814131 dated Sep. 8, 2016.
Office Action from Chinese Patent Application No. 201410359730.0 dated Aug. 22, 2016 (with English Translation).
Examiner's Report from Canadian Patent Application No. 2720601 dated Aug. 16, 2016.
Office Action from U.S. Appl. No. 13/188,327 dated Oct. 20, 2016.
Office Action from U.S. Appl. No. 12/626,355 dated Jul. 2, 2015.
Examination Report from Australian Patent Application No. 2012285492 dated Jul. 15, 2015.
Supplemental European Search Report from EPO Appl. No. EP 12 81 4131 dated Mar. 12, 2015.
Office Action from Chinese Patent Application No. 201280044120.0 dated Sep. 6, 2015.
Office Action from U.S. Appl. No. 13/188,319 dated Sep. 28, 2015.

(56) References Cited

OTHER PUBLICATIONS

Office Action dated Nov. 14, 2017 from U.S. Appl. No. 14/830,714.
Office Action dated Sep. 7, 2017 from U.S. Appl. No. 13/188,327.
Office Action dated Jun. 29, 2017 from U.S. Appl. No. 14/135,416.
Office Action dated Jul. 20, 2017 from Chinese Patent Application No. 201410359730.0 (English Translation).
Office Action dated May 30, 2017 from Canadian Patent Application No. 2720601.
Office Action dated May 31, 2017 from Chinese Patent Application No. 201280044120.0 (Machine Translation).
International Preliminary Report on Patentability from PCT/US2015/045972, dated Feb. 21, 2017.
Office Action from Chinese Patent Application No. 20140359730.0, dated Feb. 20, 2017.
Office Action from Korean Patent Application No. 10-2010-0115392 dated Nov. 15, 2016.
Advisory Action from U.S. Appl. No. 14/135,416 dated Dec. 15, 2016.
Examiner's Report from Canadian Patent Application No. 2,845,061 dated Dec. 19, 2016.

\* cited by examiner

PRE-CUT STRIPS OF KINESIOLOGY TAPE

CROSS-REFERENCE TO RELATED APPLICATIONS

This application is a continuation-in-part of, and claims the benefit of and priority to, U.S. patent application Ser. No. 12/626,355, entitled "BODY-ADHESIVE KINESIOLOGY TAPE" filed on Nov. 25, 2009, which application is incorporated herein by reference in its entirety.

U.S. patent application Ser. No. 12/626,355 claims the benefit of and priority to U.S. Provisional Patent Application Ser. No. 61/200,400, entitled "Body-Adhesive Kinesiology Tape for Sports and Medical Use and Methods and Processes Related Thereto" filed on Nov. 26, 2008, which application is incorporated herein by reference in its entirety.

This application is related to co-pending U.S. application Ser. No. 13/188,327, filed on Jul. 21, 2011, entitled, "ELASTIC STRAND FOR USE IN KINESIOLOGY TAPE", which application is incorporated herein by reference in its entirety.

This application is related to co-pending U.S. application Ser. No. 13/188,319, filed on Jul. 21, 2011, entitled, "MANUFACTURE OF KINESIOLOGY TAPE", which application is incorporated herein by reference in its entirety.

Co-pending U.S. application Ser. No. 13/188,319, filed on Jul. 21, 2011, entitled, "MANUFACTURE OF KINESIOLOGY TAPE", is a continuation-in-part of, and claims the benefit of and priority to, U.S. patent application Ser. No. 12/254,203 filed on Sep. 4, 2009, now U.S. Pat. No. 8,216,415, issued Jul. 10, 2012, which application is incorporated herein by reference in its entirety.

BACKGROUND OF THE INVENTION

Kinesiology tape consists of a fabric that includes elastic and non-elastic fibers, usually covered in cotton, which is placed on human skin. Kinesiology tape is useful in therapy to reduce soreness in overused and injured muscles and in rehabilitation to accelerate recovery. The tape can have a lifting effect on the skin which can reduce swelling and inflammation by improving circulation and reduce pain by taking pressure off pain receptors.

Nevertheless, there are a number of drawbacks in the current art regarding kinesiology tape. In particular, in order to provide proper support to various muscle groups or body parts, body-adhesive tapes must be applied in specific ways, which often requires that multiple strips of specific sizes and shapes be utilized. However, kinesiology tapes are generally available as a roll and the user must remove from the roll of tape the correct amount and, at times, cut the piece further, to allow the tape to properly support joints or muscles.

Body-adhesive kinesiology tapes for athletic use are required to be strong, resiliently elastic, and resistant to tearing in order to provide adequate support to a user. Such tapes cannot be easily torn into smaller pieces, but must be carefully cut into a desired size and shape. This requires that scissors be used to cut the tape into the desired shape and size. However, the scissors must be quite sharp, as the tape does not readily cut. This presents a danger to the user, as they may have to carry these scissors with them to the gym or other place of use.

Further, cutting the kinesiology tape can leave edges on the kinesiology tape with sharp corners. Since kinesiology tape is often used on or near joints, these sharp corners may continually poke or otherwise irritate the user. Moreover, the cut edges of the tape may begin to fray because of the cut. This may cause the kinesiology tape to become loose while the user is participating in some physical activity. Alternatively, the user may be required to reapply the kinesiology tape during some break in the activity to ensure that the tape does not become loose or fall off.

Additionally, different joints and muscle groups may require different applications of kinesiology tape. Indeed, one joint or muscle group may need different configurations of kinesiology tape for different injuries to the joint or muscle group. Therefore, the user may need to be aware of the proper method of application as well as the type and length of kinesiology tape to apply.

Thus, those with access to professional personnel, such as personal trainers or physical therapists are able to utilize the benefits of kinesiology tapes. However, those without access to such personnel, such as a person making a casual trip to the gym, or due to other time, location or access reasons are not able to enjoy these benefits.

This can prevent casual users from receiving the support benefits from such tapes. A casual user may lack the means to cut the tape and the knowledge of the different shapes and sizes of the particular strips of tape required to support a particular body area may not be readily apparent.

Accordingly, the design of a body adhesive kinesiology tape that could be applied in multiple useful conformations without the need for custom cutting and fitting would be an improvement in the art.

BRIEF SUMMARY OF SOME EXAMPLE EMBODIMENTS

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

One example embodiment includes a pre-cut strip of kinesiology tape. The pre-cut strip of kinesiology tape includes a fabric. The fabric includes a weave of fibers, where the fibers include an elastic fiber covered by a covering material. The fabric also includes a first end and a second end, where the second end is opposite the first end. The fabric further includes one or more rounded corners. The pre-cut strip of kinesiology tape also includes a longitudinal cut in the fabric. The longitudinal cut passes through at least a portion of the fabric and extends from the first end to a pre-determined distance from the second end. The pre-cut strip of kinesiology tape also includes adhesive on a first surface of the fabric, where the adhesive is configured to adhere the fabric to a human body.

Another example embodiment includes a pre-cut strip of kinesiology tape. The pre-cut strip of kinesiology tape includes a fabric. The fabric includes a weave of fibers, where the fibers include an elastic fiber covered by a covering material. The fabric is approximately rectangular in shape and includes rounded corners on all exterior corners. The pre-cut strip of kinesiology tape also includes a longitudinal cut in the fabric. The longitudinal cut passes through at least a portion of the fabric and extends from a first edge of the fabric to a pre-determined distance from a second edge of the fabric, where the first edge is opposite the second edge. The pre-cut strip of kinesiology tape also includes adhesive on a first surface of the fabric, where the adhesive is applied in a step frequency wave pattern. The step-frequency wave pattern includes a sine wave pattern with modified peaks. The adhesive is configured to adhere the fabric to a human body. The pre-cut strip of kinesiology tape also includes a backing material on the first surface of the fabric, where the backing material is configured to cover the adhesive and protect the adhesive from drying until a user is ready to apply the fabric to the human body.

Another example embodiment includes a set of pre-cut strips of kinesiology tape. The set of pre-cut strips of kinesiology tape includes two or more strips of kinesiology tape. Each of the two or more strips of kinesiology tape includes a fabric. The fabric includes a weave of fibers. The weave of fibers includes a first set of fibers oriented in a first direction and a second set of fibers oriented in a second direction, where each of the fibers in the second set of fibers include an elastic fiber covered in a covering material. The fabric is approximately rectangular in shape and includes rounded corners on each exterior corner and includes adhesive on a first surface of each of the two or more strips of kinesiology tape, where the adhesive is applied in a step frequency wave pattern. The step-frequency wave pattern includes a sine wave pattern with modified peaks. The adhesive is configured to adhere each of the two or more strips of kinesiology tape to a human body. The set of pre-cut strips of kinesiology tape also includes a backing material. The backing material includes a perforation, where the perforation is configured to permit a user to detach a first portion of the backing material from a second portion of the backing material. The backing material also includes at least one of the two or more strips of kinesiology tape adhered to the first portion of the backing material. The backing material further includes at least one of the two or more strips of kinesiology tape adhered to the second portion of the backing material.

These and other objects and features of the present invention will become more fully apparent from the following description and appended claims, or may be learned by the practice of the invention as set forth hereinafter.

BRIEF DESCRIPTION OF THE DRAWINGS

To further clarify various aspects of some example embodiments of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF SOME EXAMPLE EMBODIMENTS

Reference will now be made to the figures wherein like structures will be provided with like reference designations. It is understood that the figures are diagrammatic and schematic representations of some embodiments of the invention, and are not limiting of the present invention, nor are they necessarily drawn to scale.

In addition to providing support, body-adhesive kinesiology tapes are used by athletes for the enhancement of athletic performance and are used by athletes and non-athletes for the reduction of muscle soreness, to aid in healing from injury and in the prevention of injury. Upon application to body parts with the skin pulled taut, after returning the skin to an un-stretched position the elastic properties of body-adhesive kinesiology tapes provide an outward stretching or "lifting" force on the skin, providing enhanced fluid flow from the taped area by assisting in the opening of the lymphatic system and microcapillaries in the subcutaneous layers. Additionally, this stretching force can provide a counterbalance to muscle strain.

Figure 1:
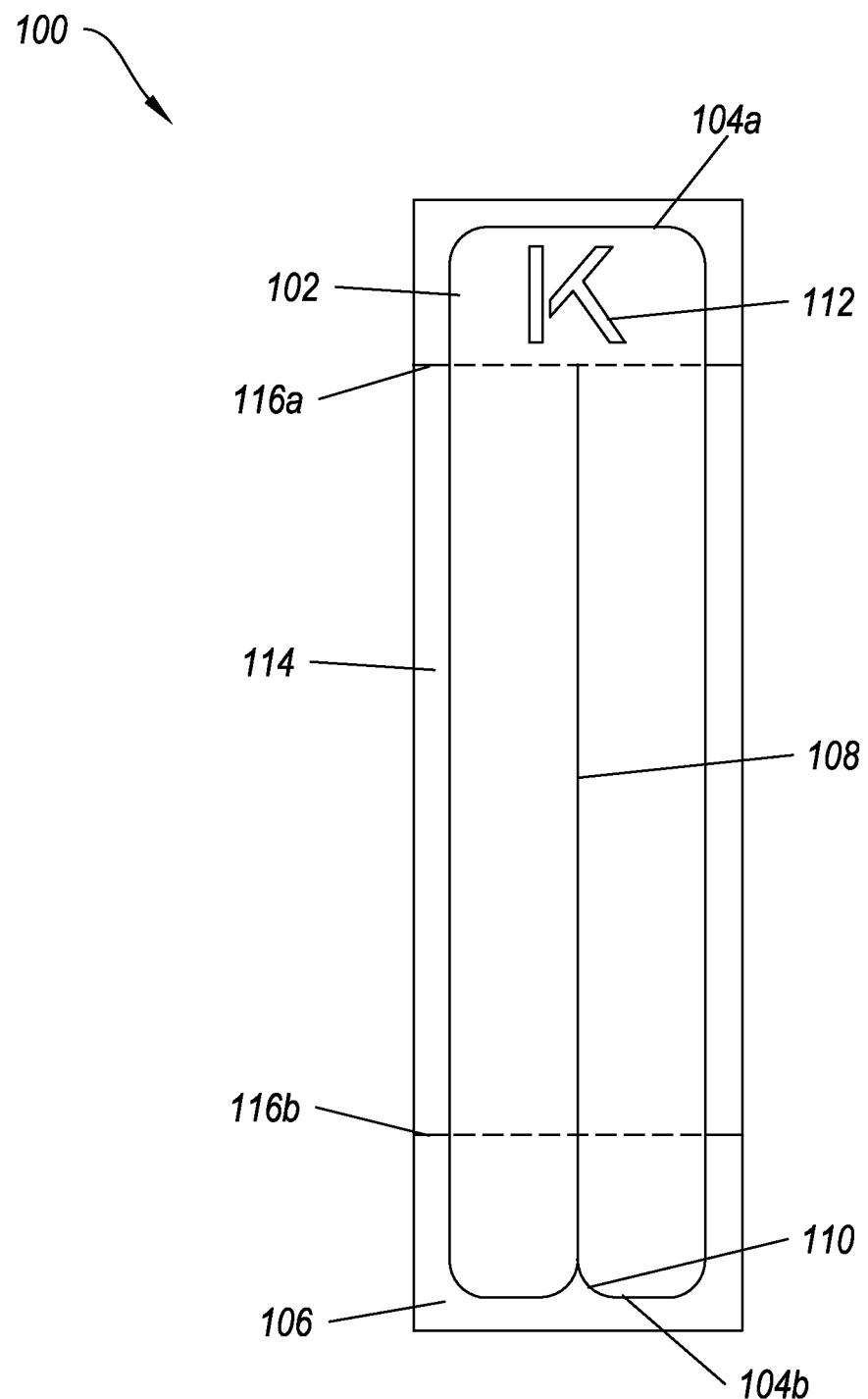
FIG. 1 illustrates an example of kinesiology tape.

FIG. 1 illustrates an example of kinesiology tape 100. In at least one implementation, kinesiology tape 100 consists of a strip of elastic and non-elastic fibers, each covered in a material which can include cotton, which is placed on human skin. The individual fibers are woven together to produce a cloth-like tape that is able to stretch in any direction. In particular, kinesiology tape 100 is useful in therapy to reduce soreness in overused and injured muscles, in rehabilitation to accelerate recovery and in the prevention of future injury. The kinesiology tape 100 can have a lifting effect on the skin which can reduce swelling and inflammation by improving circulation and reduce pain by taking pressure off pain receptors.

FIG. 1 shows that the kinesiology tape 100 can include a fabric 102. In at least one implementation, the fabric 102 can include any network of natural or artificial fibers including textiles and cloth. In at least one implementation, the fibers can include thread or yarn. For example, yarn can be produced by spinning raw wool fibers, linen, cotton, or other material on a spinning wheel to produce long strands. The fabric 102 can be formed by weaving, knitting, crocheting, knotting, or pressing fibers together, such as in felt. One of skill in the art will appreciate that the fabric 102 can include a single fiber or more than one fiber.

FIG. 1 shows that the fabric 102 can include an approximately rectangular shape. In particular, the kinesiology tape 100 extends in a longitudinal direction from a first end 104a to a second end 104b (collectively "ends 104"). The width and length of the kinesiology tape 100 can be changed as desired for particular applications. For example, the width can be in the range of from about 1 inch to about 3 inches, with a width of about 2 inches being used as the illustrative example discussed herein. Similarly, typical lengths of each individual strip may be from about 8 to about 12 inches, with a length of about 10 inches being used as the illustrative example discussed herein.

FIG. 1 also shows that the corner of the kinesiology tape 100 can include a rounded corner 106 on the external corners. As used herein, the term "external corner" shall include any corner on the exterior edge of the kinesiology tape 100 unless otherwise specified in the specification or claims. In at least one implementation, a rounded corner 106 can prevent fraying during application. Additionally or alternatively, a rounded corner 106 can reduce the chance of accidental detachment during use of the kinesiology tape 100. For example, a rounded corner 106 is much less likely than a square corner to snag on other materials, such as the user's clothing, that might detach the kinesiology tape 100 during use. Additionally or alternatively, a rounded corner 106 can provide more comfort to the user, as a rounded corner 106 does not have a sharp corner that can poke the user or otherwise cause discomfort.

FIG. 1 further shows that the kinesiology tape 100 can include a longitudinal cut 108. In at least one implementation, the longitudinal cut 108 can allow a user to split a portion of the kinesiology tape 100 when applying the kinesiology tape 100 to the user's body, as described below. The longitudinal cut 108 can extend from the second end 104b longitudinally into the body of the tape section progressing toward the first end 104a. In particular, the longitudinal cut 108 can extend to a termination point prior to the first end 104a, such that an uncut portion of tape is disposed at the second end 104b. For example, the longitudinal cut 108 can extend from the second end 104b to a point approximately two inches from the first end 104a.

In at least one implementation, the longitudinal cut 108 can pass completely through the kinesiology tape 100 or can pass through only a portion of the kinesiology tape 100. I.e., the longitudinal cut 108 can pass through only part of the width of the kinesiology tape 100. A longitudinal cut 108 which passes through only a portion of the kinesiology tape 100 can prevent separation along the longitudinal cut 108 unless so desired by the user. In particular, the longitudinal cut 108 is configured to allow the user to split the kinesiology tape 100 along the longitudinal cut 108 and any mechanism which allows the user to do so is contemplated herein. For example, the longitudinal cut 108 can include a notched cut, allowing the user to easily separate the longitudinal cut 108 by the application of a separating force. In at least one implementation, a notched cut can include alternating sections which are completely cut through interspersed with sections which are not cut at all. I.e., the cut can be similar to perforations. The cut sections can be long enough that moderate force separates the kinesiology tape 100 along the longitudinal cut 108. The cut section can be between 0.06 millimeters and 0.1 millimeters long. For example, the cut section can be approximately 0.08 millimeters long.

Additionally or alternatively, the longitudinal cut 108 can be made using a ceramic blade or laser cutting, which cuts through a portion of the fibers, allowing the user to separate the longitudinal cut 108 by the application of a separating force. Additionally or alternatively, the longitudinal cut 108 can be made through the entirety of the kinesiology tape 100 and then "resealed" using adhesive. Additional information regarding the production of the longitudinal cut 108 is provided in co-pending U.S. patent application Ser. No. 13/188,319, entitled "MANUFACTURE OF KINESIOLOGY TAPE" filed Jul. 21, 2011, previously referenced.

One of skill in the art will appreciate that the kinesiology tape 100 can include more than one longitudinal cut 108. In particular, the kinesiology tape 100 can include as many longitudinal cuts 108 as necessary to perform the desired function. For example, if kinesiology tape 100 is being used to treat contusions, the kinesiology tape 100 can include 3, 4, 5 or more longitudinal cuts 108. The longitudinal cuts 108 can allow for a larger number of tails, which can be used to treat the contusion.

FIG. 1 additionally shows that the kinesiology tape 100 can include an interior corner 110 which is rounded. In at least one implementation, the rounded interior corner 110 can remove a sharp corner that can poke the user or otherwise cause discomfort to the user. For example, during application the user can split the kinesiology tape 100 along the longitudinal cut 108. This can expose the interior corner 110. Rounding the interior corner 110 can ensure that during application, and while the user is moving after application, the kinesiology tape 100 can have an absence of sharp corners.

FIG. 1 also shows that the kinesiology tape 100 can include a logo 112. In at least one implementation, the logo 112 can be used to identify the first end 104a. In particular, the presence of a logo 112 on the uncut portion of the kinesiology tape 100 can allow the user to quickly identify the first end 104a. This can aid the user in placing the kinesiology tape 100. In particular, the user can quickly and visually identify both the first end 104a and the second end 104b, which can aid in placement, as described below. Additionally or alternatively, the logo 112 can include reflective dye. In at least one implementation, the reflective dye can reflect light which strikes the logo 112. A reflective logo 112 can increase a user's safety when exercising in low light or dark conditions.

FIG. 1 also shows that the kinesiology tape 100 can include a backing material 114 disposed underneath the kinesiology tape 100. In at least one implementation, the backing material 114 is releasably attached to the kinesiology tape 100 by an adhesive layer, as described below. In particular, the backing material 114 can include paper or any other material suitable for protecting the adhesive on the kinesiology tape 100 from drying before use. For example, the backing material 114 can include a waxed paper which protects the adhesive from being removed or drying.

In at least one implementation, the backing material 114 may be formed as a continuous piece across its width, lacking a longitudinal cut which corresponds to the longitudinal cut 108 of the kinesiology tape 100. In particular, the lack of a longitudinal cut in the backing material 114 can allow the kinesiology tape 100 to be removed from the backing material 114 as one piece, without splitting the kinesiology tape down the longitudinal cut 108. This can allow the user to separate the two strips formed by longitudinal cut 108 or to leave the two strips formed by longitudinal cut 108 adjacent to one another, depending on the intended placement. In at least one implementation, the backing material 114 can be placed on the kinesiology tape 100 before longitudinal cut 108 is formed in the kinesiology tape 100. For example, longitudinal cut 108 may be formed by die cutting through the kinesiology tape 100 to the level of the backing material 114 to result in the described structures.

FIG. 1 shows that the backing material 114 can include a first perforation 116a and a second perforation 116b (collectively "perforations 116"). For example, the perforations 116 may be disposed at points about two inches from the first and second ends 104a and 104b respectively. In at least one implementation, the perforations 116 can facilitate the tearing of the backing material 114 along the perforations 116. In particular, perforations 116 can allow a portion of the backing material 114 to be removed from the kinesiology tape 100 while other portions of the backing material 114 remain on the kinesiology tape 100. This can facilitate placement of the kinesiology tape 100 by allowing the user to only work with desired sections of the kinesiology tape 100.

In at least one implementation, the backing material 114 can be placed on the kinesiology tape 100 before perforations 116 are formed in the backing material 114. For example, perforations 116 may be formed by die cutting through the backing material 114 at or near the level of the kinesiology tape 100 to result in the described structures. Additionally or alternatively, the perforations can be formed in the backing material prior to the placement of the kinesiology tape 100 on the backing material 114.

Figure 2:
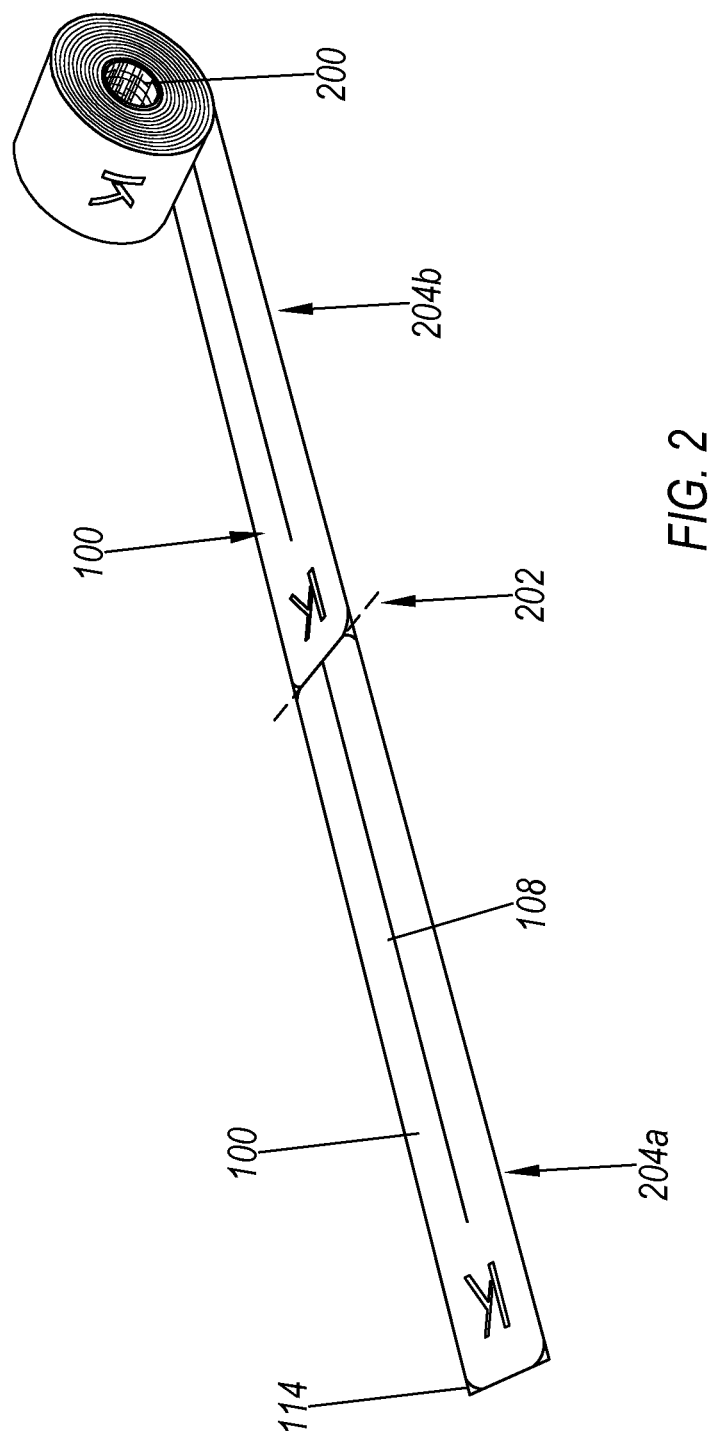
FIG. 2 illustrates a roll containing individual strips of kinesiology tape.

FIG. 2 illustrates a roll 200 containing individual strips of kinesiology tape 100. In at least one implementation, a roll 200 can be used to conveniently package a number of individual strips of kinesiology tape 100 such that a user need not cut the kinesiology tape 100. In particular, the roll 200 can include pre-cut strips of kinesiology tape 100 such that the user need not cut the kinesiology tape 100 at the time of use. Additionally or alternatively, it will be appreciated that the kinesiology tape 100 can be individually packaged as individually cut sheets, or in any other form that allows the user to access an individual strip of kinesiology tape 100 without the need to cut the kinesiology tape 100, rather than on a roll.

FIG. 2 shows that the roll 200 may include multiple strips of kinesiology tape 100. For example, the roll 200 can include individual strips of kinesiology tape 100 disposed on a single strip of backing material 114. In at least one implementation, the backing material 114 can be torn by a user for the removal of a single strip of kinesiology tape 100. Additionally or alternatively, the backing material 114 can include a perforated cut 202 across its width between each individual strip of kinesiology tape 100, creating a first portion 204a of backing material and a second portion 204b of backing material and facilitating the tearing of the backing material 114 between each individual strip of kinesiology tape 100.

In at least one implementation, the backing material 114 can be cut or perforated between strips of kinesiology tape 100 by cutting the backing material 114 with suitable dies. For example, the perforations may be made by die cuts on the backing material 114 prior to the placement of kinesiology tape 100 on the backing material 114, with subsequent placement and alignment of the kinesiology tape 100. Additionally or alternatively, a large sheet of kinesiology tape 100 can be deposited on a large sheet of backing material 114 with the backing material 114 cut after placement. For example, the kinesiology tape 100 may be formed on the backing material 114 by deposition of suitable layers of the various component materials. Additionally or alternatively, the kinesiology tape 100 can be formed then adhered to the backing material 114, as described below. The sheets of kinesiology tape 100 adhered to the backing material 114 can then undergo a series of trimming to arrive at the final product. For example, the kinesiology tape 100 can be trimmed to the desired width and length then cut into individual rolls 200, as described below.

Figure 3A:
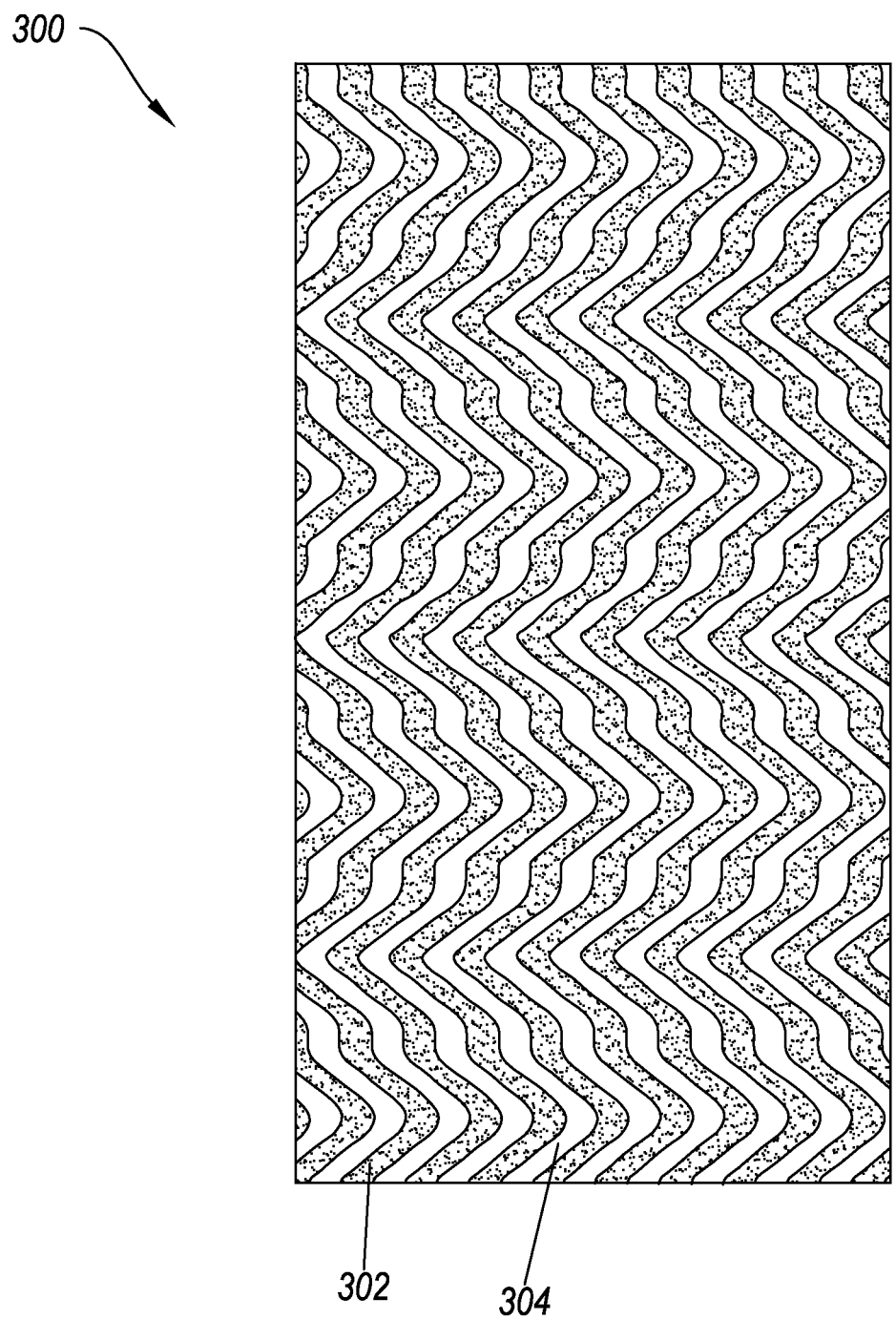
FIG. 3A illustrates an adhesive pattern for use in body-adhesive kinesiology tape.
Figure 3B:
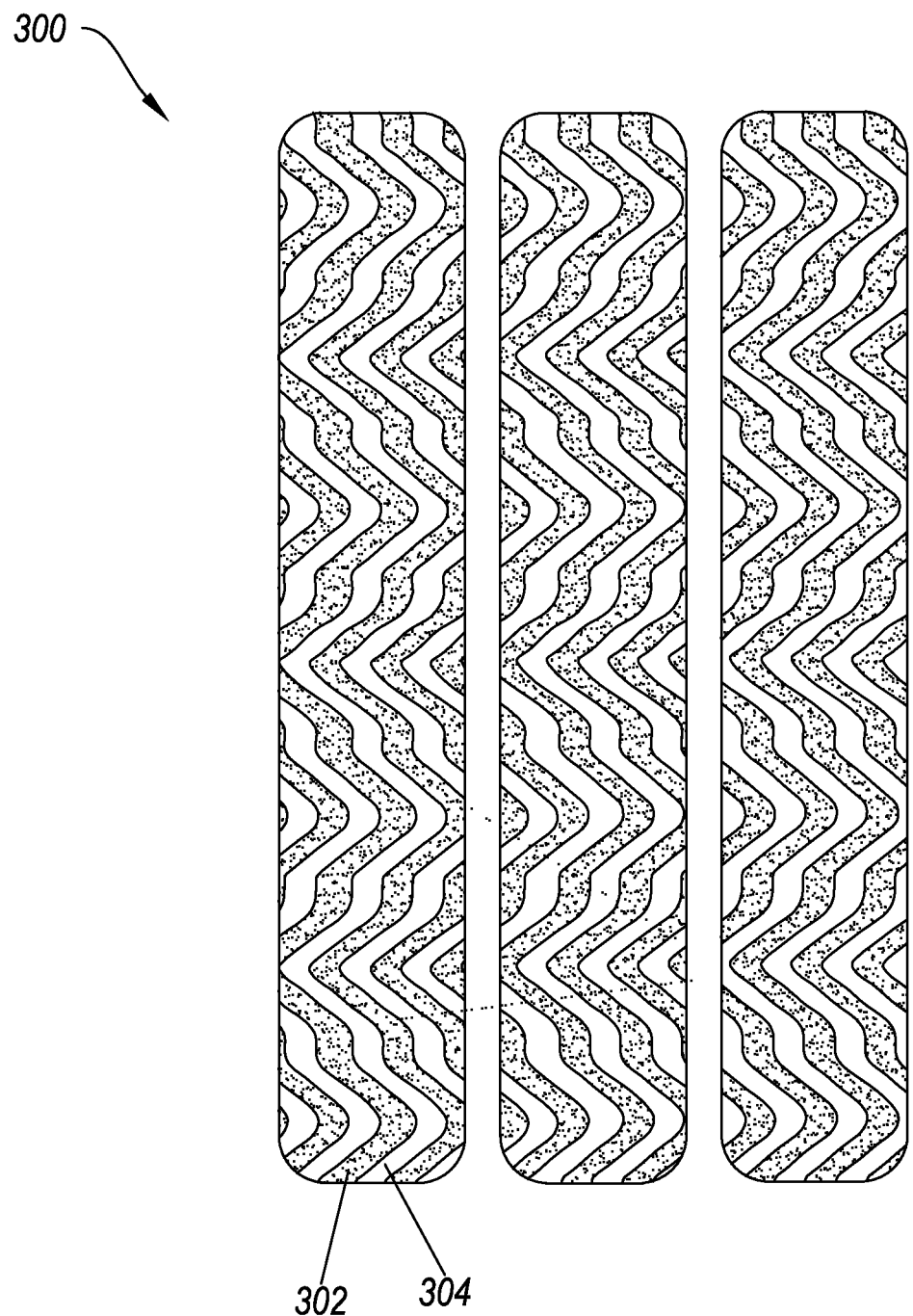
FIG. 3B illustrates the adhesive pattern of FIG. 3A after the kinesiology tape has been cut into individual strips.

FIGS. 3A and 3B illustrate an adhesive pattern 300 that can be applied to kinesiology tape. FIG. 3A illustrates the adhesive pattern 300 applied to a sheet of kinesiology tape. FIG. 3B illustrates the adhesive pattern 300 after the kinesiology tape has been cut into individual strips. Although described herein as deposited on kinesiology tape, one of skill in the art will understand that the adhesive can be applied to a backing material with kinesiology tape later applied to the backing material or through some other method.

In at least one implementation, the adhesive can include any adhesive which will allow the kinesiology tape to adhere to the skin of a user without irritating the user's skin. In at least one implementation, the adhesive can allow the kinesiology tape to adhere to the user's skin without irritating the user's skin. In particular, the main ingredient can include a single compound or a mixture of compounds. For example, the main ingredient can include polyacrylate. Additionally or alternatively, the adhesive can include a solvent which is configured to evaporate or break down after application of the adhesive, leaving the main ingredient behind. For example the adhesive can include about 50% of the main ingredient with the rest of the adhesive comprising solvent. In at least one implementation, the solvent can include ethyl acetate.

Additionally or alternatively, the adhesive can include pressure-sensitive adhesive. Pressure sensitive adhesive is adhesive which forms a bond when pressure is applied. I.e., no solvent, water, activator chemicals, heat or other activating agent is needed to activate the adhesive. In at least one implementation, the degree of bonding is influenced by the amount of pressure which is used to apply the adhesive to the surface of the backing material. I.e., pressure applied to the backing material and kinesiology tape in combination after the application of the adhesive can be used to activate the adhesive.

FIGS. 3A and 3B show that the adhesive pattern 300 can include a step frequency pattern. In at least one implementation, a step-frequency pattern can include the adhesive applied in a modified sine wave pattern. For example, the adhesive pattern 300 includes a wave with the upper peaks (as shown in FIG. 3) modified to include a higher amplitude that includes a sharper peak. Additionally, the adhesive pattern 300 includes lower peaks (as shown in FIG. 3) modified to include a higher absolute amplitude, i.e., a higher amplitude relative to the baseline of the sine wave. In at least one implementation, the adhesive pattern 300 can provide greater adhesion for the kinesiology tape. For example, the adhesive pattern 300 can provide adhesion even with lateral movement of the kinesiology tape relative to the user's skin. In particular, the adhesive pattern 300 can provide resistance to lateral movement of the kinesiology tape in any direction on the user's skin. In at least one implementation, such resistance can allow the kinesiology tape to better provide benefits to the user during use of the kinesiology tape, as described above.

In at least one implementation, the adhesive pattern 300 can be produced using an erratic cam. Additional information regarding the use of an erratic cam to produce an adhesive pattern is provided in co-pending U.S. patent application Ser. No. 13/188,319, entitled "MANUFACTURE OF KINESIOLOGY TAPE," filed Jul. 21, 2011, previously referenced.

FIGS. 3A and 3B also show that the adhesive pattern includes a series of adhesive lines 302 interrupted by gaps 304. In at least one implementation, the gaps 304 can allow the kinesiology tape to breathe. That is, the gaps 304 can allow air to reach the skin of the user. Additionally or alternatively, the gaps 304 can allow sweat from the user's skin to be wicked away from the skin by the kinesiology tape. Removing sweat from the user's skin can prevent the sweat from adversely affecting the adhesion of the kinesiology tape to the user's skin.

Figure 4:
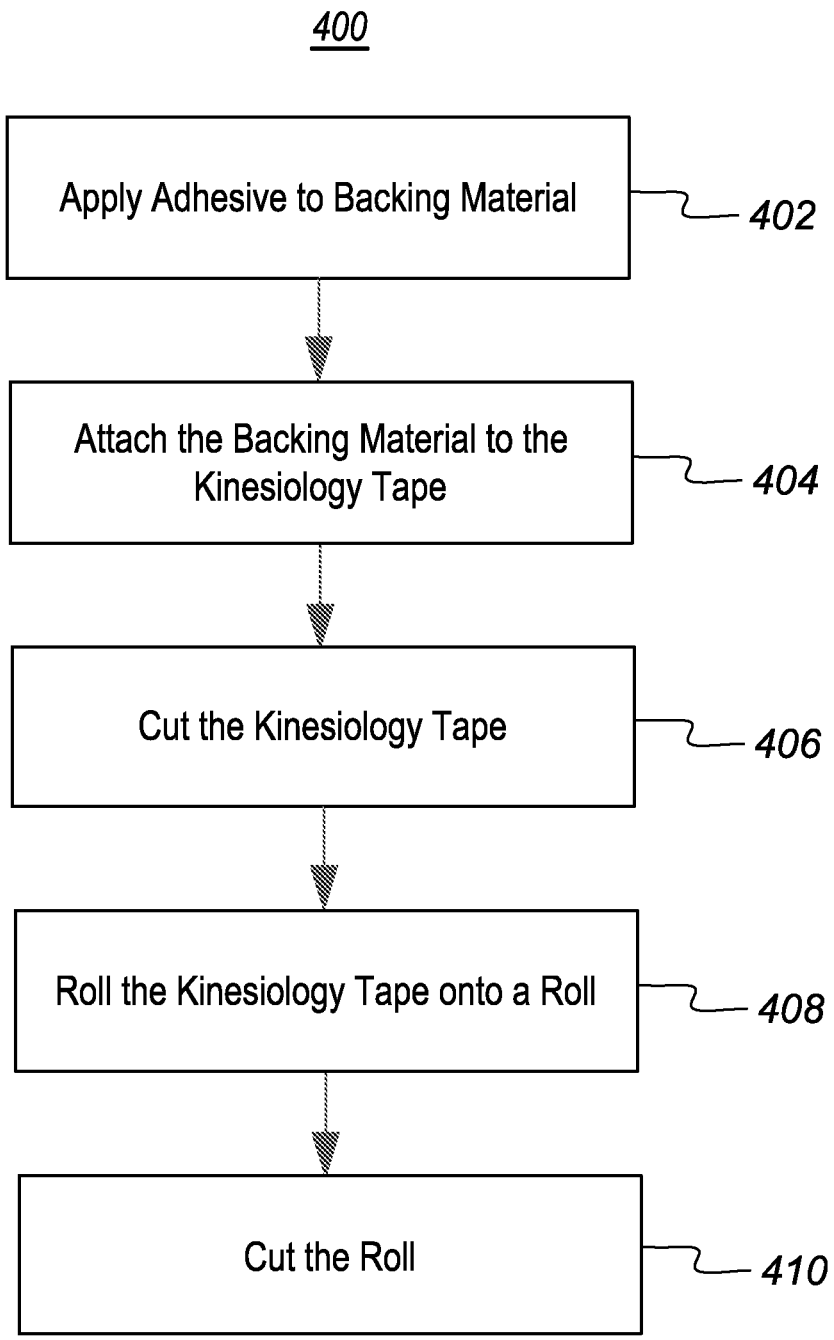
FIG. 4 is a flow chart illustrating a method for manufacturing kinesiology tape.

FIG. 4 is a flow chart illustrating a method 400 for manufacturing kinesiology tape. In at least one implementation, the kinesiology tape can be individual strips of kinesiology tape, such as the kinesiology tape 100 of FIGS. 1-3. Therefore, the method 400 will be described, exemplarily, with reference to the kinesiology tape 100 of FIGS. 1-3. Nevertheless, one of skill in the art can appreciate that the method 400 can be used to produce kinesiology tape other than the kinesiology tape 100 of FIGS. 1-3.

FIG. 4 shows that the method 400 includes applying 402 adhesive to the backing material 114. For example, the adhesive can be applied in a step frequency pattern, such as step frequency pattern 300. In at least one implementation, the adhesive can be applied to a large sheet of backing material 114. The backing material 114 can protect the adhesive and prevent drying of the solvent until a user is ready to apply the kinesiology tape 100.

FIG. 4 also shows that the method 400 includes attaching 404 the backing material 114 to kinesiology tape 100. For example, attaching 404 the backing material 114 to kinesiology tape 100 can include pressing a strip of kinesiology tape 100 onto the backing material 114 after the application of the adhesive to the backing material 114. In at least one implementation, attaching 404 the backing material 114 to kinesiology tape 100 can include applying pressure to the kinesiology tape 100 and backing material 114 to activate a pressure sensitive adhesive, as described above.

FIG. 4 further shows that the method 400 includes cutting 406 the kinesiology tape 100. In at least one implementation, cutting 406 the kinesiology tape 100 can include using a die cut, such as a roller die. In at least one implementation, the die cut can shape and form a strip of kinesiology tape 100 and the backing material 114 attached to the kinesiology tape 100 into any desired shape. In particular, the die cut can trim a sheet of kinesiology tape 100 into large ribbons of kinesiology tape 100 and trim the large ribbons of kinesiology tape 100 into individual strips of kinesiology tape 100. Additionally or alternatively, the die cut can cut or perforate the backing material 114, allowing a user to separate individual strips of kinesiology tape 100 from one another as needed or to remove only a portion of the backing material 114, as described above.

FIG. 4 also shows that the method 400 includes rolling 408 the kinesiology tape 100 onto a roll. In at least one implementation, the sheet of backing material 114 and the individual strips of kinesiology tape 100 may be rolled 408 onto a roll until the roll includes the desired number of individual strips of kinesiology tape 100 with the backing material 114 subsequently cut so that the roll includes a single strip of backing with an attached number of individual strips of kinesiology tape. For example, the roll can include any number of individual strips of kinesiology tape, such as 10, 12, 15 or 20.

In at least one implementation, the roll can include any material sufficiently strong to allow the kinesiology tape 100 to be wound around without damaging the roll. For example, the roll can include cardboard, paperboard or corrugated fiberboard. In at least one implementation, the roll allows the user to easily remove a single strip of kinesiology tape 100 and conveniently store the remaining strips of kinesiology tape 100 for later use.

FIG. 4 further shows that the method 400 further includes cutting 410 the roll. In at least one implementation, the roll can include a number of rows of individual strips of kinesiology tape 100 side-by-side. The roll can then be cut 410 into narrow rolls that include only a single strip of backing material 114 with attached kinesiology tape in a single row for packing.

Figure 5:
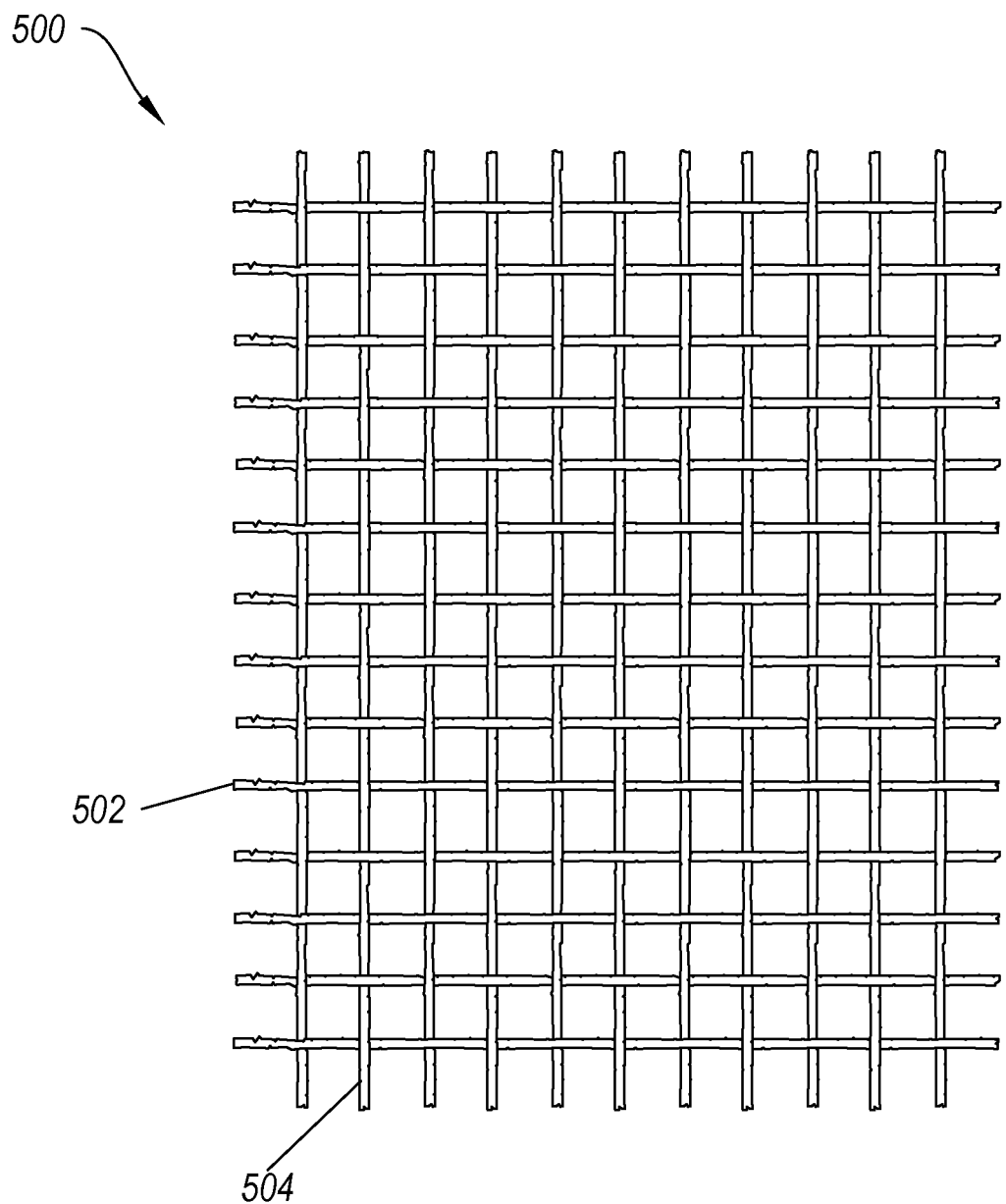
FIG. 5 illustrates an example of a weave.

FIG. 5 illustrates an example of a weave 500. FIG. 5 shows that the weave 500 can include a first set of fibers 502. FIG. 5 also shows that the weave 500 can include a second set of fibers 504. In at least one implementation, the second set of fibers 504 can be elastic. FIG. 5 further shows that the first set of fibers 502 and the second set of fibers 504 can be used to form a grid. In at least one implementation, the first set of fibers 502 and the second set of fibers 504 can be woven together.

Figure 6:
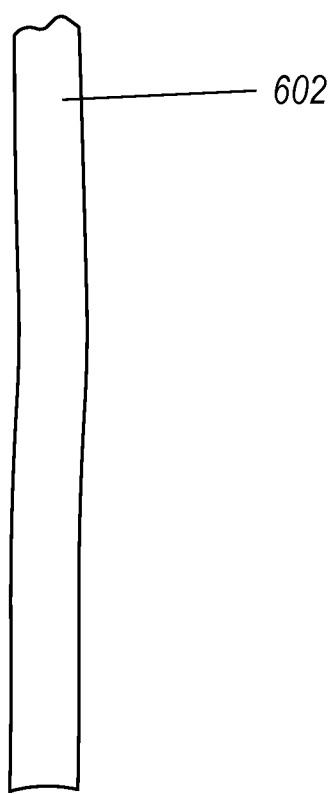
FIG. 6 illustrates an example of an elastic fiber.

FIG. 6 illustrates an example of an elastic fiber 602. FIG. 6 also shows that the elastic fiber 602 can include a covering material 604. For example, the covering material 604 can include cotton.

Figure 7:
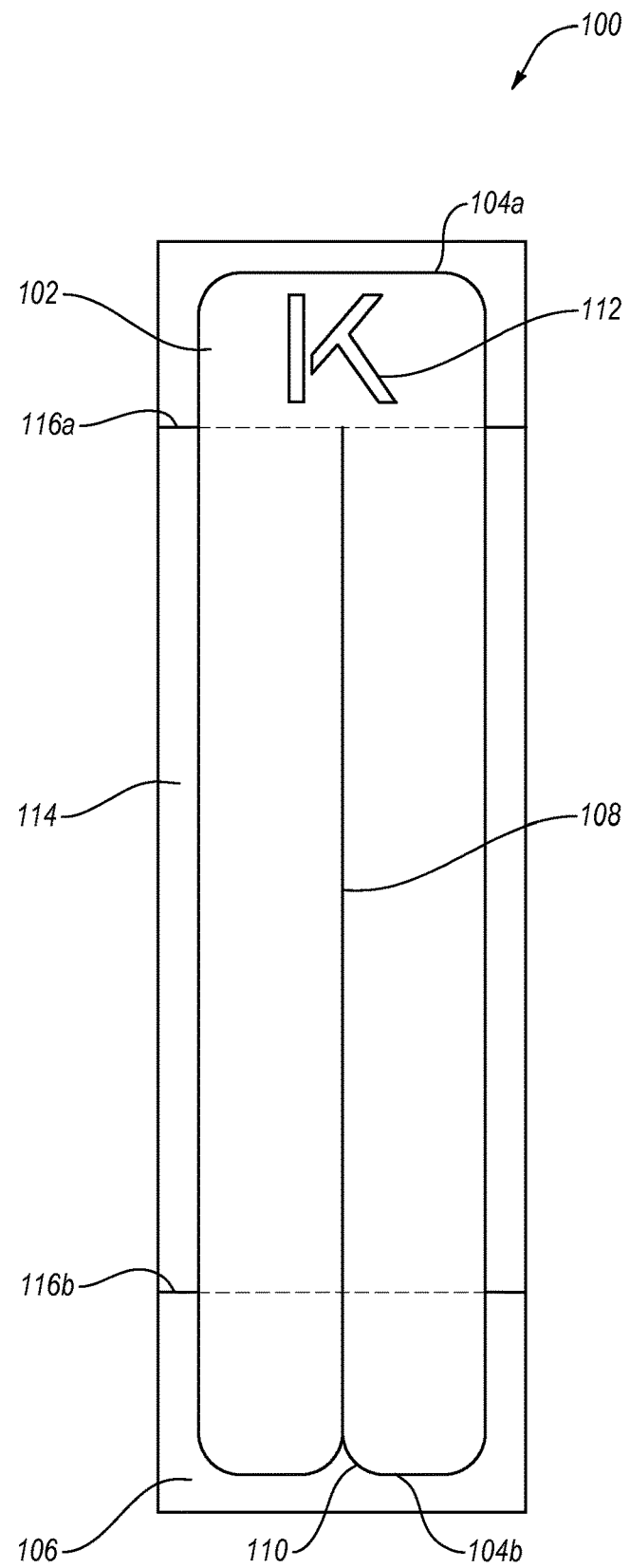
FIG. 7 illustrates an example of a strip of kinesiology tape with the longitudinal cut.

FIG. 7 illustrates an example of a strip of kinesiology tape 100 with a longitudinal cut 702a and a second longitudinal cut 702b resealed by application of an adhesive 704.

Figure 8:
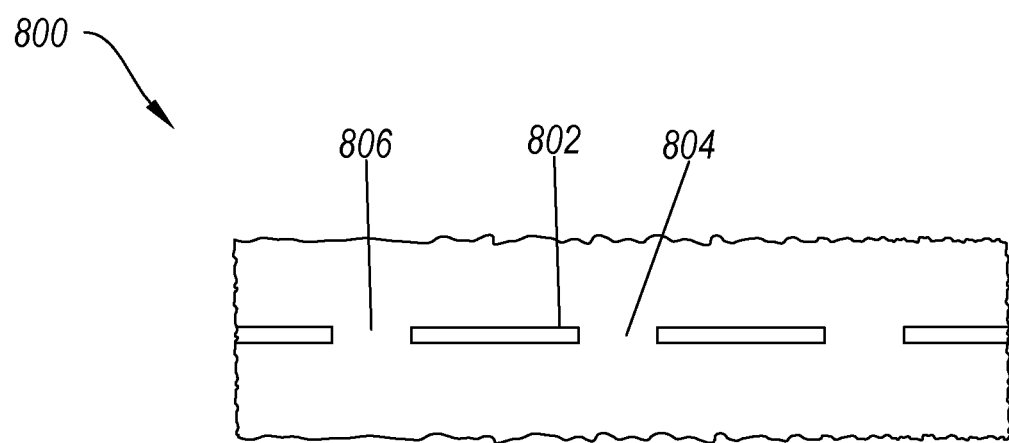
FIG. 8 illustrates a notched cut.

FIG. 8 illustrates a notched cut 800. In at least one implementation, the notched cut 800 can include a first section 802. All fibers in the first section 802 are cut. The notched cut 800 can also include a second section 804 adjacent to the first section 802 which includes one or more fibers left uncut. The notched cut 800 can further include a third section 806 adjacent to the first section 802 which includes one or more fibers left uncut.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Examples of Body-Adhesive Kinesiology Tape Applications

By way of example, and not by way of limitation, examples will be provided showing how body-adhesive kinesiology tape can be used to treat various injuries. These examples can use the kinesiology tape 100 of FIG. 1. Therefore, the example will be explained in relation to the kinesiology tape 100 of FIG. 1.

For use, the individual strips of kinesiology tape 100 can be utilized for taping a variety of body areas, without the need for a cutting implement for the kinesiology tape 100. The individual strip could be applied as a single sheet, or the uncut portion could be applied as an "anchor" portion followed by separation of the cut portion (i.e., the portion separated by longitudinal cut 108) to form various Y-shaped conformation applications. The anchor can be easily identified by the user as containing the logo 112. The various perforations of the backing material 114 can facilitate such placement by allowing removal of only some of the backing material 114 to expose only a portion of adhesive during application. Packages of kinesiology tape 100 can include instructions for users on the correct methods of applying the tape to various joints or other body areas.

Additionally or alternatively, individual packages of kinesiology tape 100 can be provided as targeted kits intended for the application of kinesiology tape 100 to a specific body area. Such kits can include instructions for users on the correct ways to apply the tape strips therein to the particular joint or body area targeted by that kit. For example, a kit for addressing tennis elbow can include two strips of kinesiology tape 100 and a set of instructions for the proper placement of the strips.

For segmental pain over a vertebrae or lower spinal pain the user can bend directly over with his head toward his toes. The user can tear the kinesiology tape along the longitudinal cut 108 such that the kinesiology tape 100 forms a "y". While in the bent over position, the user can place the anchor of the y shaped strip of kinesiology tape 100 at the base of the lower back with the two tails of the y pointing toward the user's shoulder. The user can pull each end of the kinesiology tape 100 up along each side of the center of the user's back along each edge of the spine with low to medium tension.

For mid-line neck pain, the user can tear a five to six inch piece of kinesiology tape 100 along the longitudinal cut 108. The user can place the y shaped piece of kinesiology tape with the anchor of kinesiology tape 100 in the center of the user's back between the user's shoulder blades and pull both tails up vertically along the back and base of the neck along each edge of the user's spine. The user can place a second three to four inch strip of kinesiology tape 100 from the base of the lower right side of the neck to the opposite side with full tension in the middle but no tension on the two ends.

For lumbar spine pain in the lower back, the user can lean over slightly, as if leaning over a table. The user can place a three to four inch long strip of kinesiology tape 100 horizontally across the location of pain on the user's lower back, centering the middle of the kinesiology tape 100 over the point of pain. The first strip can be placed using middle tension. Middle tension is acquired by stretching tight the middle 2 inches of the kinesiology tape 100 and placing it firmly on the target location. The edges of the kinesiology tape 100 are then placed down without tension. Tension is found only in the center of the kinesiology tape 100. The user can place a second strip of three to four inch long kinesiology tape 100 vertically across the location of the pain on the user's lower back, centering the middle of the kinesiology tape 100 over the point of pain and using the middle tension. The placement of the first strip and second strip can create a "+" sign. The user can place a third strip of three to four inch long kinesiology tape 100 along one of the diagonal axes of the first strip and second strip with the center of the third strip of kinesiology tape 100 over the main location of pain and using the middle tension. The user can continue by placing a fourth strip of three to four inch long kinesiology tape 100 along the other diagonal axis, by once again keeping the center of kinesiology tape 100 over the point of pain and using the middle tension.

For wrist extensor pain, the user can tear a sixteen to twenty inch piece of kinesiology tape 100 along the longitudinal cut 108. The user can place the anchor of the kinesiology tape 100 above the elbow and slightly on the back of the user's arm. The user can pull the ends of the kinesiology tape 100 and wrap the tails along the top of the user's forearm until the tails of the kinesiology tape 100 are slightly below the user's wrist.

For tennis elbow, the user can tear a ten to twelve inch piece of kinesiology tape 100 along the longitudinal cut 108. The user can place the anchor of the kinesiology tape 100 on the middle top of the user's forearm and pull the first tail of the kinesiology tape 100 up the user's arm. The user can pull the second tail around the user's elbow to the back of the user's elbow. The user can place a second, six to seven inch long, strip of kinesiology tape 100 with the anchor of kinesiology tape 100 right below the user's elbow on the user's forearm and wrap both ends up around the user's arm muscle.

For shin splints (also known as medial tibial stress syndrome or MTSS), the user can place a five to six inch long strip of kinesiology tape 100 with the anchor in the arch of the user's foot. The user can pull the kinesiology tape 100 up the user's leg. The kinesiology tape 100 can be placed with one edge along the interior edge of the user's tibia.

For anterior knee pain, the user can raise his/her knee slightly and place a pillow under his/her knee. The user can place a first strip of kinesiology tape 100, seven to eight inches long, horizontally right below the knee cap with middle tension. The middle of the first strip should be right below the user's knee cap. The user can tear a second, ten to eleven inch long, strip of kinesiology tape 100 along the longitudinal cut 108. The user can place the anchor of the second strip of kinesiology tape 100 on the side of the user's knee. The user can pull the first tail of the second strip along the bottom of the user's knee cap and the second tail of the second strip along the top of the user's knee cap with full tension. The first tail and the second tail can cross one another on the side of the user's knee cap opposite the anchor of the second strip.

For general shoulder pain, the user can tear a ten to eleven inch strip of kinesiology tape 100 along the longitudinal cut 108. The user can place the anchor of the kinesiology tape 100 just below the user's deltoid. The user can place the first tail of the kinesiology tape 100 along the front of the user's chest. The user can place the second tail of the kinesiology tape 100 around the back of the user's shoulder. The user can place a second, five to six inch long, strip of kinesiology tape 100 over the shoulder with full tension. The second strip can contact both tails of the first strip of kinesiology tape 100.

Alternatively, for general shoulder pain, the user can tear a sixteen to eighteen inch strip of kinesiology tape 100 along the longitudinal cut 108. The user can place the anchor of the strip over the user's shoulder along the boney edge of the shoulder. The anchor of the kinesiology tape 100 can be placed slightly in front of the shoulder with a two inch anchor and stretched over the shoulder with significant tension. The first tail of the kinesiology tape 100 can be stretched along the top edge of the user's scapula until it approaches the user's spine. The user can place the second tail just below the first tail.

For top of shoulder pain or AC separation the user can bend his/her elbow at a 90 degree angle and rest it on a table. The user can place a first three to four inch long strip of kinesiology tape 100 horizontally across the user's shoulder from the user's chest to the user's back using middle tension. The user can place a second strip of three to four inch long strip of kinesiology tape 100 orthogonal to the first strip using middle tension. The placement of the first strip and second strip should create a "+" sign. The user can place a third strip of three to four inch long kinesiology tape 100 along one of the diagonal axes of the first strip and second strip with the center of the third strip of kinesiology tape 100 over the shoulder using middle tension. The user can continue by placing a fourth strip of three to four inch long kinesiology tape 100 along the other diagonal axis, by once again keeping the center of kinesiology tape 100 over the shoulder and using middle tension.

For shoulder pain or neck soreness the user can flex his/her neck by stretching his/her head opposite the direction of the pain. The user can tear a five to six inch strip of kinesiology tape 100 along the longitudinal cut 108. The user can place the anchor of the kinesiology tape 100 pointed down near the top interior corner of the user's scapula. The user can pull both tails of the strip of kinesiology tape 100 up towards the neck with full tension. The user can place a second three to four inch strip of kinesiology tape 100 using full tension on the middle portion of the first strip of kinesiology tape 100 and place the second strip orthogonally across the first strip of kinesiology tape 100 with the center of the kinesiology tape 100 placed over the point of pain and soreness.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A pre-cut strip of kinesiology tape which a user need not cut before using the kinesiology tape, the pre-cut strip of kinesiology tape comprising:
   a fabric comprising a weave of elastic and inelastic fibers, the fabric resistant to tearing, elastic along a length of the pre-cut strip of kinesiology tape and in-elastic along a width of the pre-cut strip of kinesiology tape, the pre-cut strip of kinesiology tape sized and configured to support muscles and improve circulation when applied to a user, the pre-cut strip of kinesiology tape including elastic properties that provide an outward lifting effect on the skin when applied to a user;
   adhesive on a first surface of the fabric, the adhesive configured to adhere the fabric to a human body, the adhesive applied in a step frequency wave pattern including a plurality of steps along a longitudinal length of the fabric, the step frequency wave pattern including a series of adhesive lines and gaps, the step frequency wave pattern comprising a modified sine wave pattern with modified peaks relative to a baseline sine wave, the modified peaks including upper peaks with a higher amplitude and a sharper peak than the baseline sine wave, the modified peaks including lower peaks with a higher amplitude and a sharper peak than the baseline sine wave; and
   a backing material on the first surface of the fabric, the backing material configured to cover the adhesive and protect the adhesive from drying until a user is ready to apply the fabric to the human body;
   wherein, when applied to a user, the pre-cut strip of kinesiology tape is not intended to fix in place or prevent movement of the user.

2. The pre-cut strip of kinesiology tape as in claim 1, further comprising a first perforation in the backing material to facilitate tearing of the backing material to allow a portion of the backing material to be removed from the kinesiology tape while another portion of the backing material remains.

3. The pre-cut strip of kinesiology tape as in claim 2, wherein removing the portion of the backing material facilitates placement of the kinesiology tape by allowing a user to only work with desired portions of the kinesiology tape.

4. The pre-cut strip of kinesiology tape as in claim 2, further comprising a second perforation in the backing material.

5. The pre-cut strip of kinesiology tape as in claim 1, further comprising a logo to identify an end of the pre-cut strip of kinesiology tape and to aid the user in placing the pre-cut strip of kinesiology tape, the logo visually identifying a first end of the pre-cut strip of kinesiology tape, the first end of the pre-cut strip of kinesiology tape intended to be first applied to a user and then a second end of the pre-cut strip of kinesiology tape is intended to be applied to the user.

6. The pre-cut strip of kinesiology tape as in claim 5, wherein the logo includes reflective dye.

7. The pre-cut strip of kinesiology tape as in claim 1, wherein the weave of fibers comprises a first set of fibers orientated in a first direction and a second set of fibers orientated in a second direction; and
   wherein the second set of fibers includes an elastic fiber and a covering material covering the elastic fiber.

8. The pre-cut strip of kinesiology tape as in claim 1, further comprising a longitudinal cut disposed in the fabric, the longitudinal cut extending a pre-determined distance.

9. The pre-cut strip of kinesiology tape as in claim 1, wherein the weave of fibers comprises an elastic fiber covered by a covering material.

10. The pre-cut strip of kinesiology tape as in claim 1, further comprising:
    a longitudinal cut extending through at least a portion of the fabric, the longitudinal cut extending from a first end of the pre-cut strip of kinesiology tape towards a second end of the pre-cut strip of kinesiology tape;
    a first rounded corner of the fabric extending from the first end of the pre-cut strip of kinesiology tape to the longitudinal cut; and
    a second rounded corner of the fabric extending from the first end of the pre-cut strip of kinesiology tape to the longitudinal cut.

11. The pre-cut strip of kinesiology tape as in claim 1, further comprising a set of pre-cut strips of kinesiology tape, the set of pre-cut strips of kinesiology tape including two or more pre-cut strips of kinesiology tape.

12. The pre-cut strip of kinesiology tape as in claim 1, wherein the fibers comprise artificial fibers.

13. The pre-cut strip of kinesiology tape as in claim 1, further comprising a longitudinal cut that is sized and configured to allow a user to split a portion of the kinesiology tape when applying the kinesiology tape to a user, the longitudinal cut passing completely through the kinesiology tape.

14. The pre-cut strip of kinesiology tape as in claim 1, further comprising a longitudinal cut that is sized and configured to allow a user to split a portion of the kinesiology tape when applying the kinesiology tape to a user, the longitudinal cut passing through only a portion of the kinesiology tape to prevent unintentional separation along the longitudinal cut.

15. The pre-cut strip of kinesiology tape as in claim 1, further comprising a plurality of longitudinal cuts, each longitudinal cut of the plurality of cuts sized and configured to allow a user to split a portion of the kinesiology tape when applying the kinesiology tape to a user.

16. The pre-cut strip of kinesiology tape as in claim 1, further comprising a longitudinal cut disposed in the fabric, the longitudinal cut passing through a portion of the fabric, the longitudinal cut not severing the backing material.

17. The pre-cut strip of kinesiology tape as in claim 1, further comprising a first perforation that perforates a first portion of the backing material, the first perforation sized and configured to facilitate tearing of the backing material along the first perforation.

18. The pre-cut strip of kinesiology tape as in claim 1, further comprising a first perforation cut across a width of the backing material.

19. A pre-cut strip of kinesiology tape which a user need not cut before using the kinesiology tape, the pre-cut strip of kinesiology tape comprising:
    a fabric comprising a weave of elastic and inelastic fibers, the fabric resistant to tearing, elastic along a length of the pre-cut strip of kinesiology tape and in-elastic along a width of the pre-cut strip of kinesiology tape, the pre-cut strip of kinesiology tape sized and configured to support muscles and improve circulation when applied to a user, the pre-cut strip of kinesiology tape including elastic properties that provide an outward lifting effect on the skin when applied to a user;
    an adhesive on a first surface of the fabric, the adhesive applied in a step frequency wave pattern including a plurality of steps along a longitudinal length of the fabric, the step frequency wave pattern comprising a series of adhesive lines and gaps, the step frequency wave pattern comprising a modified sine wave pattern with modified peaks relative to a baseline sine wave, the modified peaks including upper peaks with a higher amplitude and a sharper peak than the baseline sine wave, the modified peaks including lower peaks with a higher amplitude and a sharper peak than the baseline sine wave; and a backing material on the first surface of the fabric, the backing material configured to cover the adhesive and protect the adhesive from drying until a user is ready to apply the pre-cut strip of kinesiology tape.

20. A pre-cut strip of kinesiology tape which a user need not cut before using the kinesiology tape, the pre-cut strip of kinesiology tape comprising:

a fabric comprising a weave of fibers, the fabric resistant to tearing, elastic along a length of the pre-cut strip of kinesiology tape and in-elastic along a width of the pre-cut strip of kinesiology tape, the pre-cut strip of kinesiology tape sized and configured to support muscles and improve circulation when applied to a user, the pre-cut strip of kinesiology tape providing a lifting effect on the skin to enhance fluid flow when applied to the user;

adhesive on a first surface of the fabric, the adhesive configured to adhere the fabric to a human body, the adhesive applied in a step frequency wave pattern including a plurality of steps along a longitudinal length of the fabric, the step frequency wave pattern including a series of adhesive lines and gaps, the gaps covering at least about fifty percent (50%) of the first surface of the fabric, the step frequency wave pattern comprising a modified sine wave pattern with modified peaks relative to a baseline sine wave, the modified peaks including upper peaks with a higher amplitude and a sharper peak than the baseline sine wave, the modified peaks including lower peaks with a higher amplitude and a sharper peak than the baseline sine wave; and a backing material on the first surface of the fabric, the backing material configured to cover the adhesive and protect the adhesive from drying until a user is ready to apply the fabric to the human body.

* * * * *